(12) United States Patent
Murali

(10) Patent No.: US 6,197,306 B1
(45) Date of Patent: Mar. 6, 2001

(54) HERBAL COMPOSITION FOR THE TREATMENT OF CHRONIC OBSTRUCTIVE PULMONARY DISEASE, BRONCHITIS AND RESPIRATORY DISORDERS AND A PROCESS FOR PREPARING THE SAME

(75) Inventor: Panchapagesa Muthuswamy Murali, Calcutta (IN)

(73) Assignee: Dalmia Centre for Biotechnology, Coimbatore, Tamil Nadu (IN)

( * ) Notice: Subject to any disclaimer, the term of this patent is extended or adjusted under 35 U.S.C. 154(b) by 0 days.

(21) Appl. No.: 09/271,883

(22) Filed: Mar. 18, 1999

(30) Foreign Application Priority Data

Mar. 23, 1998 (IN) ............................................. 475/CAL/98

(51) Int. Cl.$^7$ .................................................. A01N 65/00
(52) U.S. Cl. ............................................................. 424/195.1
(58) Field of Search ........................................... 424/195.1

(56) References Cited

U.S. PATENT DOCUMENTS 4,440,760    4/1984    Newnham .

OTHER PUBLICATIONS

Promt Computer Abstract 97:405087 "Homeolab all Natural Homeophatic Medicine–Cough and Cold Syrup" Product Alert (Jul. 14, 1997).*

\* cited by examiner

Primary Examiner—Herbert J. Lilling
(74) Attorney, Agent, or Firm—Mishrilal Jain

(57) ABSTRACT

The present invention defines a herbal composition for the treatment of chronic obstructive pulmonary disease, bronchitis and respiratory disorders and a process for preparing the same. The composition comprises:

| | |
|---|---|
| Bryonia | |
| Ipecacuanha | 100–75% |
| Drosera | |
| and | |
| Antimony potassium tartrate | 0–24% |

The process for preparing the herbal composition comprises:

washing and cleaning the plant materials of Bryonia, Ipecacuanha and Drosera, surface sterilizing the said plant materials with sodium hypochlorite and drying, cutting the dried plant materials into small pieces individually, grinding and pulverizing the said plant materials separately, preferably of 1 mm particle size, extracting the said granulated plant materials separately in a polar solvent and evaporating the said solvent under vacuum to get the extracted materials in powder form, mixing at least two of the said extracted materials with the antimony potassium tartarate in the ratio 100–75:0–25 to prepare said desired herbal composition.

15 Claims, No Drawings

HERBAL COMPOSITION FOR THE TREATMENT OF CHRONIC OBSTRUCTIVE PULMONARY DISEASE, BRONCHITIS AND RESPIRATORY DISORDERS AND A PROCESS FOR PREPARING THE SAME

This invention relates to a herbal composition for the treatment of chronic obstructive pulmonary disease, bronchitis and respiratory disorders and the process of preparing the same.

BACKGROUND

Excess smoking irritates the bronchial tube and lowers their resistance so that they become vulnerable. It leads to a condition called bronchitis. The inflammation of the mucus membrane lining the bronchiole and bronchial tube within the chest with breathing disorder affecting the expiratory function is the characteristic feature.

In most cases of bronchitis, the larynx, trachea and bronchia tubes are acutely inflamed. The tissues are swollen due to irritation. Large quantities of mucus are secreted and poured into the windpipe to protect the inflamed mucus membrane. The phlegm, when expelled is found to be viscid and purulent. There is usually a high fever, some difficulty in breathing and deep chest cough. Other symptoms are hoarseness and pain in the chest and loss of appetite. Breathing trouble continuous till the inflammation subsides and mucus is removed.

Chronic Obstructive Pulmonary Disease (COPD) features progressive chronic airflow obstruction due to chronic bronchitis, emphysema or both. The obstruction of airflow may be partly reversible and some patients may manifest bronchial hyper-responsiveness.

There are several Indian traditional medicines recommended for treatment. For instance Cofdry, Kolet and Zecuf The composition of these medicines are given below:

|  | Cofdry (10 ml contains) | Koflet (5 ml contains) | Zecuf (10 ml contains) |
| --- | --- | --- | --- |
| Curcuma longu | — | 50 mg | — |
| Tulsi | 200 mg | 100 mg | 100 mg |
| Yasthimadhu | 50 mg | 100 mg | 60 mg |
| Haridra | — | — | 50 mg |
| Shunthi | — | — | 10 mg |
| Vasaka | 200 mg | 200 mg | 60 mg |
| Brahati | — | — | 20 mg |
| Push kammool | — | — | 20 mg |
| Sugdha muricha | — | — | 10 mg |
| Vibhitaka | — | 50 mg | — |
| Viola odorata | — | — | 20 mg |
| Grita Kunari and Pepermint salt | — | — | 6 mg |
| Ocimum santum | 200 mg | — | — |
| Zingiber offiundi | — | 25 mg | — |
| Solanum xantho carpum | 100 mg | — | — |
| S. Irilobatum | 50 mg | — | — |
| Glycynhiya glabra | 50 mg | — | — |
| Alpinia chinensis | 50 mg | — | — |
| Cinnanomum zylanica | 25 mg | — | — |
| C. tanda | 25 mg | — | — |
| Piper longum | 25 mg | 20 mg | — |
| Myristica fragrans | 25 mg | — | — |
| Cubeba officinalis | 25 mg | — | — |
| Cinnamomum canphora | 10 mg | — | — |
| Termindig bellerica | — | 200 mg | — |
| Pudina phool | — | — | — |
| Mentha arvensi | — | 3 mg | — |
| Eucalyphis Oil | — | 2 mg | — |
| Syrup | — | — | — |
| Navsagar (NH$_4$Cl$_2$) | — | 30 mg | — |

The above medicines are not effective against chronic obstructive pulmonary disease, bronchitis and respiratory disorder.

The object of this invention is to provide a simple but effective composition for treatment of chronic obstructive pulmonary disease, bronchitis and respiratory disorder.

To achieve the said objective this invention provides a process of preparing a herbal composition for the treatment of Chronic Obstructive Pulmonary Disease (COPD), bronchitis and respiratory disorders comprising:

washing and cleaning the plant materials of Bryocnia, Ipecacuanha and Drosera, surface sterilizing the said plant materials with sodium hypochlorite and drying, cutting the dried plant materials into small pieces individually, grinding and pulverizing the said plant materials separately, preferably of 1 mm particle size, extracting the said granulated plant materials separately in a polar solvent and evaporating the said solvent under vacuum to get the extracted materials in powder form, mixing at least two of the said extracted materials with the antimony potassium tartarate in the ratio 100–75:0–25 to prepare said desired herbal composition.

The solvent used are ketones, alcohols, esters, ethers, nitryles, amides, sulfoxides, substituted aliphatic hydrocarbons, aromatic hydrocarbons and substituted aromatic hydrocarbons and mixtures thereof preferably acetone, benzene, dichloromethane, ethanol, ethyl acetate, ethylene dichloride, methanol, methyl acetate, methyl t-butyl ether, methyl formate, 2-propanol, toluene and xylene and mixture thereof.

The present invention also relates to a herbal composition A herbal composition for the treatment of chronic obstructive pulmonary disease, bronchitis and respiratory disorders comprising:

| | |
| --- | --- |
| Bryonia | 100–75% |
| Ipecacuanha | |
| Drosera | and |
| Antimony potassium tartrate | 0–25% |

The fruit and the roots of the plant material of the plant Bryonia are used. Only roots of the plant material of the plant Ipecacuanha and Drosera are used.

The antimony potassium tartrate used is of the formula $C_8H_4K_2O_{12}Sb_2 \cdot 3H_2O$ having molecular weight 667.86

The said extracted materials used in the formation of composition with antimony potassium tartrate are in the following proportion by wt.:

| | |
|---|---|
| Bryonia | 100–75% |
| Ipecacuanha | |
| Drosera | |
| and | |
| Antimony potassium tartrate | 0–25% | or

The said extracted materials used in the formation of composition with antimony potassium tartrate are in the following proportion by wt.:

| | |
|---|---|
| Bryonia | 90–80% |
| Ipecacuanha | |
| Drosera | |
| and | |
| Antimony potassium tartrate | 10–20% | or

The said extracted materials used in the formation of composition with antimony potassium tartarate are in the following proportion by wt.:

| | |
|---|---|
| Bryonia | 25% |
| Ipecacuanha | 25% |
| Drosera | 25% |
| and | |
| Antimony potassium tartrate | 25% | or

The said extracted materials used in the formation of composition with antimony potassium tartarate are in the following proportion by wt.:

| | |
|---|---|
| Bryonia | 35% |
| Ipecacuanha | 25% |
| Drosera | 30% |
| and | |
| Antimony potassium tartrate | 10% | or

The said extracted materials used in the formation of composition with antimony potassium tartrate are in the following proportion by wt.:

| | |
|---|---|
| Bryonia | |
| Ipecacuanha | 100–75% |
| and | |
| Antimony potassium tartrate | 0–25% | or

The said extracted materials used in the formation of composition with antimony potassium tartarate are in the following proportion by wt.:

| | |
|---|---|
| Bryonia | 35% |
| Ipecacuanha | 45% |
| and | |
| Antimony potassium tartrate | 20% | or

The said extracted materials used in the formation of composition with antimony potassium tartrate are in the following proportion by wt.:

| | |
|---|---|
| Bryonia | 90–80% |
| Ipecacuanha | |
| and | |
| Antimony potassium tartrate | 10–20% | or

The said extracted materials used in the formation of composition with antimony potassium tartrate are in the following proportion by wt.:

| | |
|---|---|
| Bryonia | 40% |
| Ipecacuanha | 45% |
| and | |
| Antimony potassium tartrate | 15% | or

The said extracted materials used in the formation of composition with antimony potassium tartrate are in the following proportion by wt.:

| | |
|---|---|
| Bryonia | 100–75% |
| Drosera | |
| and | |
| Antimony potassium tartrate | 0–25% | or

The said extracted materials used in the formation of composition with antimony potassium tartrate are in the following proportion by wt.:

| | |
|---|---|
| Bryonia | 35% |
| Drosera | 55% |
| and | |
| Antimony potassium tartrate | 10% | or

The said extracted materials used in the formation of composition with antimony potassium tartrate are in the proportion by wt.:

| | |
|---|---|
| Ipecacuanha | 100–75% |
| Drosera | |
| and | |
| Antimony potassium tartrate | 0–25% | or

The said extracted materials used in the formation of composition with antimony potassium tartrate are in the proportion by wt.:

| Ipecacuanha | 35% |
|---|---|
| Drosera | 45% |
| and | |
| Antimony potassium tartrate | 20% |

The description of plants is given below for easy identification. It is important that the right species is identified correctly for this preparation.

Bryonia—(Kattuthumatikai)
Description of Plants

Perennial scabrid monecious tendrillar herb with slender angled stem; leaves depply, palmately five lobed, scabrid on both sides, hispid on the tlerves beneath and rounded at the apex; the male flowers yellow in small clusters on slender globosc; fruits ellipsoid or sub-globosc, yellow or yellow with green stripes; seeds while, ellipsoid.

Ipecacuanha—(Poaya)
Description of Plants

Half-shrubby perennial, roots several, scarcely branched, orange-brown. Leaves few, somewhat crowded at the upper part of the stem, opposite, shortly stalked, stipples large, united at the base, where are several ovoid glands, persistent, pressed to the stem, whitish, about as long as the petiole, deeply cut into four subulate aciniae, blade 24 inches long or more, oval, acute or blunt at the apex, entire and more or less wavy on the margin, thick, with a few hairs on the edge, dark green and nearly smooth above, paler, somewhat pubescent and with prominent veins beneath. Flowers small, sessile, about 10–20 together, in a dense head supported on a cylindrical, pubescent, purplish, axillary but apparently terminal peduncle. Surrounded by an involucre of four ovate, entire, downy, enequal bracts; a small acute pubescebt bract accompanies each flower. Calyx adherent, downy, the limb free, of 5 short, triangular-ovate, acute. Corolla funnel-shaped, hairy outside, stamens 5, inserted at about the middle of the tube, Ovary inferior, with a fleshy epigynous disck on the top, 2 celled. Fruit several in a small cluster at the end of the reflexed penduncle, fleshy, smooth, shining, deep purple-violet. Seed solitary in each pyrene.

Drosera—(Chitra)
Description of Plants

Erect herb; stems erect, slender, minutely glandular, leafy, 10–30 cm., often branching. Leaves alternate, half-moon-shaped, about 6 mm across, peltate, upper surface and margins beset with viscid, flandular hairs; radical leaves smaller, rosulate, soon disappearing. Flowers 2-sexual, regular, white, 6 mm.diam., in terminal, branching racemes. Calyx 5-parted; segments glandular, minutely toothed. Petals 5, entire. Stamens 5. Ovary free, ovoid, 1-celled; style 3; stigmas terminal, minutely gringed; ovules numerous. Capsule enclosed within the persistent calyx and corolla, 3-valved; seeds minute, attached to the valves.

ANTIMONY POTASSIUM TARTARATE

Molecular formula—$C_8 H_4 K_2 O_{12} Sb_2 \cdot 3H_2O$

Molecular weight—667.86

Transparent crystals (effervescence on exposure to air) or powder, sweetish metallic taste. Poisonous one gram dissolved in 12 ml water, 3 ml boiling water, 15 ml of glycerol. Insoluble in alcohol

PREPARATION OF THE PLANT MATERIAL FOR EXTRACTION

Bryonia (Kattuthumattikai)

Fruit—The fruit is harvested when still not ripe. The fruit is gently excised, the seeds totally removed. The pulp and rind is shade dried. The dried material is carefully ground in a grinder and sieved in a mesh of size.

Root—The entire plant is carefully uprooted and the rhyzophere is gently excised. The excised root material is carefully washed and brushed several times to remove soil particles and other contamination. Gentle surface sterilization using sodium hypoclorite is conducted. The material is then shade dried. After drying the material is cut into small bits and powdered using grinder. The ground material is then seived.

Ipecacunha (Ipecacuanha)

The entire plant is carefully uprooted and the rhyzophere is gently excised. The excised root material is carefully washed and brushed several times to remove soil particles and other contaminations. Gentle surface sterilization using sodium hypochlorite is conducted. The material is then shade dried. The material is cut into small bits and powdered using a grinder. The ground material is then sieved.

Drosera (Drosera)

The entire plant is uprooted and washed. Then gentle surface sterilization using sodium hypochlorite is conducted. The material is shade dried and ground with the help of a coffee grinder. The ground material is then passed through a mesh

EXTRACTION PROTOCOL FOR THE PLANT MATERIAL

Each of the above material is independently extracted with ethanol—the preferred solvent. A wide variety of other solvents may also be used with good results.

Steps

A. The extraction steps involves the following:

The plant material ground to the mesh size of 1 mm is put in a soxlet apparatus.

The solvent is poured into the vessel and extracted for 48 hours with the system temperature never exceeding 55° C.

After several passes of the extract of solvent over the material, the solvent is evaporated in roto-vacuum flask (or evaporated under vacuum).

The remaining material is generally in a powder form. Extracts from all the three plants are separately collected for the purpose of formulation.

The invention will now be described with reference to the following examples:

EXAMPLE I

Take 100 g of each plant materials of Bryonia, Ipecacuanha and Drosera, wash clean and cut into pieces. Grind and pulverize into 1 mm pieces. Extract the powder with ethanol and evaporate extract in a 'rotovac' to obtain the dry powder extract of each of the plant material. Mixing the said powder in the following proportion:

| Bryonia | 25% |
|---|---|
| Ipecacuanha | 25% |

-continued

| | |
|---|---|
| Drosera | 25% |
| Antimony potassium tartrate | 25% |

The mixed formulation is either encapsulated or made into tablets or formulate in honey. Each capsule contains 250 mg of the formulation. The same is true for the tablet with the honey based syrup. The formulation is adjusted to deliver 250 mg of the above formulation in 6 ml of honey

EXAMPLE II

Take 100 g of each plant materials of Bryonia, Ipecacuanha and Drosera, wash clean and cut into pieces. Grind and pulverize into 1 mm pieces. Extract the powder with ethanol and evaporate extract in a 'rotovac' to obtain the dry powder extract of each of the plant material. Mixing the said powder in the following proportion:

| | |
|---|---|
| Bryonia | 30% |
| Ipecacuanha | 35% |
| Drosera | 35% |
| Antimony potassium tartrate | 0% |

The mixed formulation is either encapsulated or made into tablets or formulate in honey. Each capsule contains 250 mg of the formulation. The same is true for the tablet with the honey based syrup. The formulation is adjusted to deliver 250 mg of the above formulation in 6 ml of honey

EXAMPLE III

Take 100 g of each plant materials of Bryonia, Ipecacuanha and Drosera, wash clean and cut into pieces. Grind and pulverize into 1 mm pieces. Extract the powder with ethanol and evaporate extract in a 'rotovac' to obtain the dry powder extract of each of the plant material. Mixing the said powder in the following proportion:

| | |
|---|---|
| Bryonia | 40% |
| Ipecacuanha | 25% |
| Drosera | 25% |
| Antimony potassium tartrate | 10% |

The mixed formulation is either encapsulated or made into tablets or formulate in honey. Each capsule contains 250 mg of the formulation. The same is true for the tablet with the honey based syrup. The formulation is adjusted to deliver 250 mg of the above formulation in 6 ml of honey.

EXAMPLE IV

Take 100 g of each plant materials of Bryonia and Ipecacuanha, wash clean and cut into pieces. Grind and pulverize into 1 mm pieces. Extract the powder with ethanol and evaporate extract in a 'rotovac' to obtain the dry powder extract of each of the plant material. Mixing the said powder in the following proportion:

| | |
|---|---|
| Bryonia | 35% |
| Ipecacuanha | 45% |
| Antimony potassium tartrate | 20% |

The mixed formulation is either encapsulated or made into tablets or formulate in honey. Each capsule contains 250 mg of the formulation. The same is true for the tablet with the honey based syrup. The formulation is adjusted to deliver 250 mg of the above formulation in 6 ml of honey.

EXAMPLE V

Take 100 g of each plant materials of Bryonia and Drosera, wash clean and cut into pieces. Grind and pulverize into 1 mm pieces. Extract the powder with ethanol and evaporate extract in a 'rotovac' to obtain the dry powder extract of each of the plant material. Mixing the said powder in the following proportion:

| | |
|---|---|
| Bryonia | 40% |
| Drosera | 45% |
| Antimony potassium tartrate | 15% |

The mixed formulation is either encapsulated or made into tablets or formulate in honey. Each capsule contains 250 mg of the formulation. The same is true for the tablet with the honey based syrup. The formulation is adjusted to deliver 250 mg of the above formulation in 6 ml of honey.

EXAMPLE VI

Take 100 g of each plant materials of Ipecacuanha and Drosera, wash clean and cut into pieces. Grind and pulverize into 1 mm pieces. Extract the powder with ethanol and evaporate extract in a 'rotovac' to obtain the dry powder extract of each of the plant material. Mixing the said powder in the following proportion:

| | |
|---|---|
| Ipecacuanha | 35% |
| Drosera | 40% |
| Antimony potassium tartrate | 25% |

The mixed formulation is either encapsulated or made into tablets or formulate in honey. Each capsule contains 250 mg of the formulation. The same is true for the tablet with the honey based syrup. The formulation is adjusted to deliver 250 mg of the above formulation in 6 ml of honey.

The active ingredients in each of the plant material in the formulation is detected and qualified through HPLC.

TOXICOLOGICAL TEST

The composition in the highest ratio of equal proportions of all the three plants along with the slat was tested on mice. The oral LD 50 of the drug and the results are pretty encouraging. There are no adverse effects on the mice tried. A dose over 3850 mg/kg body weight is the LD 50.

DOSAGE:

For children: one capsule of 250 mg per day
For adults: two or three capsules per day depending upon the condition of the patients.

SYMPTOMS IT CAN CURE

COPD, Bronchitis, Smokers cough and cancer are the major diseases this formulation can bring about a cure. The disease symptoms were followed through monitoring a number of parameters, which is given through the Clinical Protocol. 15 patients were studied through an Ethical Committee approved protocol.

CLINICAL PROTOCOL

Overall Response to treatment with Drug DCBT 1234 as concluded by Doctor Comment

| Type | Good | Fair | Poor | Total |
|---|---|---|---|---|
| Table of Original Frequency | | | | |
| Drug | 9 | 5 | 1 | 15 |
| Placebo | 6 | 2 | 7 | 15 |
| Total | 15 | 7 | 8 | 30 |
| Expected Value | | | | |
| Drug | 7.5 | 3.5 | 4 | 15 |
| Placebo | 7.5 | 3.5 | 4 | 15 |
| Total | 15 | 7 | 8 | 30 |

$X^2 = Z(O-E)2/E = 5.41$ $d.f = V = (r-1)(c-1) = (2-1)(3-1) = 2\ d.f$ table value for 2 df at $t_{0.05} = 5.991$ $Cal\ X^2 = 5.41 < t_{0.05},\ 2\ d.f = 5.991$ We accept the hypothesis that the drug is better than the placebo in curing COPD as per Doctor's Comment.

Statistical Analysis - t test - COUGH

Comparision of Cough before and after taking drug

| Patients (n) | 0 day (x1) | 6th day (x2) | d = (x2 − x1) | d² | (x1 − Meanx1)² | (x2 − Meanx2)² | |
|---|---|---|---|---|---|---|---|
| 1 | 3 | 1 | −2 | 4 | 0.004 | 0.071 | Hypothesis (H₀): After |
| 2 | 3 | 2 | −1 | 1 | 0.004 | 0.538 | consuming drug there is no |
| 3 | 3 | 1 | −2 | 4 | 0.004 | 0.071 | significant reduction. |
| 4 | 3 | 1 | −2 | 4 | 0.004 | 0.071 | Result: Ho rejected |
| 5 | 3 | 1 | −2 | 4 | 0.004 | 0.071 | Conclusion: It is concluded that |
| 6 | 3 | 1 | −2 | 4 | 0.004 | 0.071 | there is significant reduction after |
| 7 | 2 | 1 | −1 | 1 | 0.871 | 0.071 | consuming drug. |
| 8 | 3 | 2 | −1 | 1 | 0.004 | 0.538 | Co-eff of variation before and |
| 9 | 3 | 2 | −1 | 1 | 0.004 | 0.538 | after consuming drug. |
| 10 | 3 | 1 | −2 | 4 | 0.004 | 0.071 | Result: 1. More consistent (in |
| 11 | 3 | 2 | −1 | 1 | 0.004 | 0.538 | severity) before taking drug. 2. |
| 12 | 3 | 2 | −1 | 1 | 0.004 | 0.538 | Less consistent after taking drug. |
| 13 | 3 | 0 | −3 | 9 | 0.004 | 1.604 | |
| 14 | 3 | 1 | −2 | 4 | 0.004 | 0.071 | |
| 15 | 3 | 1 | −2 | 4 | 0.004 | 0.071 | |
| | 2.93 | 1.27 | −25 | 47 | 0.933 | 4.933 | |

Mean = Sum d/n   −1.667
(Mean)²    2.778   SD   0.25   0.573
s             0.617   CV   8.50   45.28
Cal t        −10.458
table value is 2.1448 at $t_{0.05}$ at 14 d.f

Comparison of Drug Vs Placebo at the end of the 6th day

| | Cough grading | | Drug | | Placebo | | |
|---|---|---|---|---|---|---|---|
| Patients (n) | Drug (x1) | Placebo (x2) | x1 − Mean | (x1 − Mean)² | x2 − Mean | (x2 − Mean)² | |
| 1 | 1 | 1 | −0.27 | 0.071 | −1.00 | 1 | Hypothesis (H₀): After |
| 2 | 2 | 1 | 0.73 | 0.538 | −1.00 | 1 | consuming drug there is no |
| 3 | 1 | 1 | −0.27 | 0.071 | −1.00 | 1 | significant difference between |
| 4 | 1 | 2 | −0.27 | 0.071 | 0.00 | 0 | drug and placebo. |
| 5 | 1 | 1 | −0.27 | 0.071 | −1.00 | 1 | Result: Ho rejected |
| 6 | 1 | 1 | −0.27 | 0.071 | −1.00 | 1 | Conclusion: There is significant |
| 7 | 1 | 1 | −0.27 | 0.071 | −1.00 | 1 | differnce between drug and |
| 8 | 2 | 3 | 0.73 | 0.538 | 1.00 | 1 | placebo. |
| 9 | 2 | 3 | 0.73 | 0.538 | 1.00 | 1 | Co-eff of variation between |
| 10 | 1 | 3 | −0.27 | 0.071 | 1.00 | 1 | drug and placebo |

-continued

Statistical Analysis - t test - COUGH

| 11 | 2 | 1 | 0.73  | 0.538 | −1.00 | 1  | Result: 1. More consistent (less |
| 12 | 2 | 3 | 0.73  | 0.538 | 1.00  | 1  | variable) in drug. 2. Less |
| 13 | 0 | 3 | −1.27 | 1.604 | 1.00  | 1  | consistent in placebo (More |
| 14 | 1 | 3 | −0.27 | 0.071 | 1.00  | 1  | variable) |
| 15 | 1 | 3 | −0.27 | 0.071 | 1.00  | 1  | |
|    | 1.27 | 2.00 |    | 4.933 |      | 14 | | s            0.822   SD   0.573   0.966  
Cal t value  −2.442  CV   45.275  48.305  
table value is 2.0484 at $t_{0.05}$ at 28 d.f Conclusion: More uniformity among drug group patients on account of drug consumption whereas less uniformity among placebo group patients.

Statistical Analysis - t test - TEMPERATURE

Comparision of Temperature before and after taking drug

| Patients (n) | 0 day (x1) | 6th day (x2) | d = (x2 − x1) | $d^2$ | $(x1 - \text{Meanx1})^2$ | $(x2 - \text{Meanx2})^2$ | |
|---|---|---|---|---|---|---|---|
| 1  | 101.8 | 99.8  | −2    | 4     | 0.086 | 0.071 | Hypothesis ($H_o$): After |
| 2  | 102.4 | 100.2 | −2.2  | 4.84  | 0.094 | 0.444 | consuming drug there is no |
| 3  | 102.4 | 99.6  | −2.8  | 7.84  | 0.094 | 0.004 | significant reduction. |
| 4  | 102   | 99.6  | −2.4  | 5.76  | 0.009 | 0.004 | Result: Ho rejected |
| 5  | 102.4 | 99.6  | −2.8  | 7.84  | 0.094 | 0.004 | Conclusion: It is concluded that |
| 6  | 101.8 | 100.4 | −1.4  | 1.96  | 0.086 | 0.751 | there is significant reduction after |
| 7  | 101.8 | 100   | −1.8  | 3.24  | 0.086 | 0.218 | consuming drug. |
| 8  | 101.8 | 99.8  | −2    | 4     | 0.086 | 0.071 | Co-eff of variation before and |
| 9  | 101.8 | 99.6  | −2.2  | 4.84  | 0.086 | 0.004 | after consuming drug. |
| 10 | 101.6 | 99.6  | −2    | 4     | 0.243 | 0.004 | Result: 1. Less consistent (in |
| 11 | 103.8 | 99.6  | −4.2  | 17.64 | 2.913 | 0.004 | severity) before taking drug. 2. |
| 12 | 102.8 | 99.4  | −3.4  | 11.56 | 0.499 | 0.018 | More consistent after taking drug. |
| 13 | 101.2 | 98.4  | −2.8  | 7.84  | 0.798 | 1.284 | |
| 14 | 102   | 99    | −3    | 9     | 0.009 | 0.284 | |
| 15 | 101.8 | 98.4  | −3.4  | 11.56 | 0.086 | 1.284 | |
|    | 102.09 | 99.53 | −38.4 | 105.92 | 5.269 | 4.453 | |

Mean = Sum d/n          −2.560  
$(\text{Mean})^2$        6.554   SD   0.59   0.545  
s                        0.738   CV   0.58   0.55  
Cal t                    −13.443  
table value is 2.1448 at $t_{0.05}$ at 14 d.f

Comparison of Drug Vs Placebo at the end of the 6th day

| | Temp grading | | Drug | | Placebo | | |
|---|---|---|---|---|---|---|---|
| Patients (n) | Drug (x1) | Placebo (x2) | x1 − Mean | $(x1 - \text{Mean})^2$ | x2 − Mean | $(x2 - \text{Mean})^2$ | |
| 1  | 99.8  | 99.6  | 0.27  | 0.071 | −1.00 | 1    | Hypothesis ($H_o$): After |
| 2  | 100.2 | 99.8  | 0.67  | 0.444 | −0.80 | 0.64 | consuming drug there is no |
| 3  | 99.6  | 99.4  | 0.07  | 0.004 | −1.20 | 1.44 | significant difference between |
| 4  | 99.6  | 99.6  | 0.07  | 0.004 | −1.00 | 1    | drug and placebo. |
| 5  | 99.6  | 99.8  | 0.07  | 0.004 | −0.80 | 0.64 | Result: Ho rejected |
| 6  | 100.4 | 99.6  | 0.87  | 0.751 | −1.00 | 1    | Conclusion: There is significant |
| 7  | 100   | 99.6  | 0.47  | 0.218 | −1.00 | 1    | differnce between drug and |
| 8  | 99.8  | 99.6  | 0.27  | 0.071 | −1.00 | 1    | placebo. |
| 9  | 99.6  | 102   | 0.07  | 0.004 | 1.40  | 1.96 | Co-eff of variation between |
| 10 | 99.6  | 101.4 | 0.07  | 0.004 | 0.80  | 0.64 | drug and placebo |
| 11 | 99.6  | 102   | 0.07  | 0.004 | 1.40  | 1.96 | Result: 1. More consistent (less |
| 12 | 99.4  | 101.4 | −0.13 | 0.018 | 0.80  | 0.64 | variable) in drug. 2. Less |
| 13 | 98.4  | 102   | −1.13 | 1.284 | 1.40  | 1.96 | consistent in placebo (More |
| 14 | 99    | 101.8 | −0.53 | 0.284 | 1.20  | 1.44 | variable) |
| 15 | 98.4  | 101.4 | −1.13 | 1.284 | 0.80  | 0.64 | |
|    | 99.53 | 100.60 |      | 4.453 |       | 16.96 | | s            0.875   SD   0.545  1.063  
Cal t value  −3.340  CV   0.547  1.057  
table value is 2.0484 at $t_{0.05}$ at 28 d.f Conclusion: More uniformity among drug group patients on account of drug consumption whereas less uniformity among placebo group patients.

Statistical Analysis - t test - RHONCHI

Comparision of Rhonchi before and after taking drug

| Patients (n) | 0 day (x1) | 6th day (x2) | d = (x2 − x1) | $d^2$ | $(x1 - Meanx1)^2$ | $(x2 - Meanx2)^2$ | |
|---|---|---|---|---|---|---|---|
| 1 | 3 | 1 | −2 | 4 | 0.64 | 0.018 | Hypothesis ($H_o$): After |
| 2 | 3 | 1 | −2 | 4 | 0.64 | 0.018 | consuming drug there is no |
| 3 | 2 | 1 | −1 | 1 | 0.04 | 0.018 | significant reduction. |
| 4 | 3 | 1 | −2 | 4 | 0.64 | 0.018 | Result: Ho rejected |
| 5 | 2 | 1 | −1 | 1 | 0.04 | 0.018 | Conclusion: It is concluded that |
| 6 | 2 | 1 | −1 | 1 | 0.04 | 0.018 | there is significant reduction after |
| 7 | 2 | 1 | −1 | 1 | 0.04 | 0.018 | consuming drug. |
| 8 | 2 | 1 | −1 | 1 | 0.04 | 0.018 | Co-eff of variation before and |
| 9 | 2 | 1 | −1 | 1 | 0.04 | 0.018 | after consuming drug. |
| 10 | 2 | 1 | −1 | 1 | 0.04 | 0.018 | Result: 1. More consistent (in |
| 11 | 2 | 1 | −1 | 1 | 0.04 | 0.018 | severity) before taking drug. 2. |
| 12 | 2 | 1 | −1 | 1 | 0.04 | 0.018 | Less consistent after taking drug. |
| 13 | 2 | 0 | −2 | 4 | 0.04 | 0.751 | |
| 14 | 2 | 1 | −1 | 1 | 0.04 | 0.018 | |
| 15 | 2 | 0 | −2 | 4 | 0.04 | 0.751 | |
| | 2.2 | 0.87 | −20 | 30 | 2.4 | 1.733 | |

Mean = Sum d/n   −1.333
$(Mean)^2$   1.778   SD   0.4   0.340
s   0.488   CV   18.18   39.22
Cal t   −10.583
table value is 2.1448 at $t_{0.05}$ at 14 d.f

Comparison of Drug Vs Placebo at the end of the 6th day

| | Rhonchi grading | | Drug | | Placebo | | |
|---|---|---|---|---|---|---|---|
| Patients (n) | Drug (x1) | Placebo (x2) | x1 − Mean | $(x1 - Mean)^2$ | x2 − Mean | $(x2 - Mean)^2$ | |
| 1 | 1 | 0 | 0.13 | 0.018 | −1.60 | 2.56 | Hypothesis ($H_o$): After |
| 2 | 1 | 1 | 0.13 | 0.018 | −0.60 | 0.36 | consuming drug there is no |
| 3 | 1 | 1 | 0.13 | 0.018 | −0.60 | 0.36 | significant difference between |
| 4 | 1 | 1 | 0.13 | 0.018 | −0.60 | 0.36 | drug and placebo. |
| 5 | 1 | 1 | 0.13 | 0.018 | −0.60 | 0.36 | Result: Ho rejected |
| 6 | 1 | 1 | 0.13 | 0.018 | −0.60 | 0.36 | Conclusion: There is significant |
| 7 | 1 | 1 | 0.13 | 0.018 | −0.60 | 0.36 | differnce between drug and |
| 8 | 1 | 1 | 0.13 | 0.018 | −0.60 | 0.36 | placebo. |
| 9 | 1 | 2 | 0.13 | 0.018 | 0.40 | 0.16 | Co-eff of variation between |
| 10 | 1 | 3 | 0.13 | 0.018 | 1.40 | 1.96 | drug and placebo |
| 11 | 1 | 3 | 0.13 | 0.018 | 1.40 | 1.96 | Result: 1. More consistent (less |
| 12 | 1 | 3 | 0.13 | 0.018 | 1.40 | 1.96 | variable) in drug. 2. Less |
| 13 | 0 | 2 | −0.87 | 0.751 | 0.40 | 0.16 | consistent in placebo (More |
| 14 | 1 | 2 | 0.13 | 0.018 | 0.40 | 0.16 | variable) |
| 15 | 0 | 2 | −0.87 | 0.751 | 0.40 | 0.16 | |
| | 0.87 | 1.60 | | 1.733 | | 11.6 | | s   0.690   SD   0.340   0.879
Cal t value   −2.910   CV   39.223   54.962
table value is 2.0484 at $t_{0.05}$ at 28 d.f Conclusion: More uniformity among drug group patients on account of drug consumption whereas less uniformity among placebo group patients.

Statistical Analysis - t test - SPUTUM

Comparision of Sputum before and after taking drug

| Patients (n) | 0 day (x1) | 6th day (x2) | d = (x2 − x1) | $d^2$ | $(x1 - Meanx1)^2$ | $(x2 - Meanx2)^2$ | |
|---|---|---|---|---|---|---|---|
| 1 | 4 | 1 | −3 | 9 | 0.018 | 0.071 | Hypothesis ($H_o$): After |
| 2 | 4 | 1 | −3 | 9 | 0.018 | 0.071 | consuming drug there is no |
| 3 | 4 | 2 | −2 | 4 | 0.018 | 0.538 | significant reduction. |
| 4 | 4 | 2 | −2 | 4 | 0.018 | 0.538 | Result: Ho rejected |
| 5 | 4 | 2 | −2 | 4 | 0.018 | 0.538 | Conclusion: It is concluded that |

-continued

Statistical Analysis - t test - SPUTUM

|   |      |      |     |     |       |       |                                      |
|---|------|------|-----|-----|-------|-------|--------------------------------------|
| 6  | 4    | 2    | −2  | 4   | 0.018 | 0.538 | there is significant reduction after |
| 7  | 4    | 1    | −3  | 9   | 0.018 | 0.071 | consuming drug.                      |
| 8  | 4    | 1    | −3  | 9   | 0.018 | 0.071 | Co-eff of variation before and       |
| 9  | 4    | 1    | −3  | 9   | 0.018 | 0.071 | after consuming drug.                |
| 10 | 4    | 2    | −2  | 4   | 0.018 | 0.538 | Result: 1. More consistent (less     |
| 11 | 4    | 1    | −3  | 9   | 0.018 | 0.071 | uniformity) in sputum before         |
| 12 | 4    | 2    | −2  | 4   | 0.018 | 0.538 | taking drug. 2. Less                 |
| 13 | 4    | 0    | −4  | 16  | 0.018 | 1.604 | consistent (more uniformity) after   |
| 14 | 3    | 1    | −2  | 4   | 0.751 | 0.071 | taking drug.                         |
| 15 | 3    | 0    | −3  | 9   | 0.751 | 1.604 |                                      |
|    | 3.87 | 1.27 | −39 | 107 | 1.733 | 6.933 |                                      |

Mean = Sum d/n −2.600
(Mean)$^2$ 6.760  SD 0.34  0.680
s 0.632  CV 8.79  53.67
Cal t −15.922
table value is 2.1448 at $t_{0.05}$ at 14 d.f Comparison of Drug Vs Placebo at the end of the 6th day

| | Sputum quality grading | | Drug | | Placebo | | |
|---|---|---|---|---|---|---|---|
| Patients (n) | Drug (x1) | Placebo (x2) | x1 − Mean | (x1 − Mean)$^2$ | x2 − Mean | (x2 − Mean)$^2$ | |
| 1  | 1 | 1 | −0.27 | 0.071 | −1.47 | 2.151 | Hypothesis (H$_o$): After |
| 2  | 1 | 2 | −0.27 | 0.071 | −0.47 | 0.218 | consuming drug there is no |
| 3  | 2 | 2 | 0.73  | 0.538 | −0.47 | 0.218 | significant difference between |
| 4  | 2 | 2 | 0.73  | 0.538 | −0.47 | 0.218 | drug and placebo. |
| 5  | 2 | 2 | 0.73  | 0.538 | −0.47 | 0.218 | Result: Ho rejected |
| 6  | 2 | 1 | 0.73  | 0.538 | −1.47 | 2.151 | Conclusion: There is significant |
| 7  | 1 | 2 | −0.27 | 0.071 | −0.47 | 0.218 | differnce between drug and |
| 8  | 1 | 2 | −0.27 | 0.071 | −0.47 | 0.218 | placebo. |
| 9  | 1 | 2 | −0.27 | 0.071 | −0.47 | 0.218 | Co-eff of variation between |
| 10 | 2 | 3 | 0.73  | 0.538 | 0.53  | 0.284 | drug and placebo |
| 11 | 1 | 2 | −0.27 | 0.071 | −0.47 | 0.218 | Result: 1. Less consistent in |
| 12 | 2 | 4 | 0.73  | 0.538 | 1.53  | 2.351 | sputum quality in drug group. 2. |
| 13 | 0 | 4 | −1.27 | 1.604 | 1.53  | 2.351 | More consistent in placebo. |
| 14 | 1 | 4 | −0.27 | 0.071 | 1.53  | 2.351 | |
| 15 | 0 | 4 | −1.27 | 1.604 | 1.53  | 2.351 | |
|    | 1.27 | 2.47 |    | 6.933 |       | 15.733 | | s           0.900  SD 0.680  1.024
Cal t value −3.653  CV 53.674  41.520
table value is 2.0484 at $t_{0.50}$ at 28 d.f Conclusion: Less uniformity in sputum quality among drug group patients on account of drug consumption whereas more uniformity among placebo group patients.

Statistical Analysis - t test - RALES

Comparision of Rales before and after taking drug

| Patients (n) | 0 day (x1) | 6th day (x2) | d = (x2 − x1) | d$^2$ | (x1 − Meanx1)$^2$ | (x2 − Meanx2)$^2$ | |
|---|---|---|---|---|---|---|---|
| 1  | 0 | 0 | 0  | 0 | 6.418 | 0.640 | Hypothesis (H$_o$): After |
| 2  | 2 | 1 | −1 | 1 | 0.284 | 0.040 | consuming drug there is no |
| 3  | 3 | 1 | −2 | 4 | 0.218 | 0.040 | significant reduction. |
| 4  | 3 | 1 | −2 | 4 | 0.218 | 0.040 | Result: Ho rejected |
| 5  | 3 | 1 | −2 | 4 | 0.218 | 0.040 | Conclusion: It is concluded that |
| 6  | 3 | 1 | −2 | 4 | 0.218 | 0.040 | there is significant reduction after |
| 7  | 3 | 1 | −2 | 4 | 0.218 | 0.040 | consuming drug. |
| 8  | 3 | 1 | −2 | 4 | 0.218 | 0.040 | Co-eff of variation before and |
| 9  | 3 | 1 | −2 | 4 | 0.218 | 0.040 | after consuming drug. |
| 10 | 3 | 1 | −2 | 4 | 0.218 | 0.040 | Result: 1. More consistent (less |
| 11 | 3 | 1 | −2 | 4 | 0.218 | 0.040 | uniformity) in Rales before taking |
| 12 | 3 | 1 | −2 | 4 | 0.218 | 0.040 | drug. 2. Less consistent (more |
| 13 | 1 | 0 | −1 | 1 | 2.351 | 0.640 | uniformity) after taking drug. |

|  |  |  |  |  |  |  |
|---|---|---|---|---|---|---|
| Statistical Analysis - t test - RALES | | | | | | |
| 14 | 2 | 1 | −1 | 1 | 0.284 | 0.040 |
| 15 | 3 | 0 | −3 | 9 | 0.218 | 0.640 |
|  | 2.53 | 0.80 | −26 | 52 | 11.733 | 2.400 |

Mean = Sum d/n   −1.733
(Mean)$^2$   3.004   SD   0.88   0.400
s   0.704   CV   34.91   50.00
Cal t   −9.539
table value is 2.1448 at $t_{0.05}$ at 14 d.f

Comparison of Drug Vs Placebo at the end of the 6th day

|  | Rales grading | | Drug | | Placebo | | |
|---|---|---|---|---|---|---|---|
| Patients (n) | Drug (x1) | Placebo (x2) | x1 − Mean | (x1 − Mean)$^2$ | x2 − Mean | (x2 − Mean)$^2$ |  |
| 1 | 0 | 0 | −0.80 | 0.640 | −1.73 | 3.004 | Hypothesis (H$_o$): After |
| 2 | 1 | 1 | 0.20 | 0.040 | −0.73 | 0.538 | consuming drug there is no |
| 3 | 1 | 1 | 0.20 | 0.040 | −0.73 | 0.538 | significant difference between |
| 4 | 1 | 1 | 0.20 | 0.040 | −0.73 | 0.538 | drug and placebo. |
| 5 | 1 | 1 | 0.20 | 0.040 | −0.73 | 0.538 | Result: Ho rejected |
| 6 | 1 | 1 | 0.20 | 0.040 | −0.73 | 0.538 | Conclusion: There is significant |
| 7 | 1 | 1 | 0.20 | 0.040 | −0.73 | 0.538 | differnce between drug and |
| 8 | 1 | 1 | 0.20 | 0.040 | −0.73 | 0.538 | placebo. |
| 9 | 1 | 3 | 0.20 | 0.040 | 1.27 | 1.604 | Co-eff of variation between |
| 10 | 1 | 3 | 0.20 | 0.040 | 1.27 | 1.604 | drug and placebo |
| 11 | 1 | 3 | 0.20 | 0.040 | 1.27 | 1.604 | Result: 1. More consistent in |
| 12 | 1 | 3 | 0.20 | 0.040 | 1.27 | 1.604 | drug. 2. Less consistent in |
| 13 | 0 | 2 | −0.80 | 0.640 | 0.27 | 0.071 | placebo. |
| 14 | 1 | 2 | 0.20 | 0.040 | 0.27 | 0.071 |  |
| 15 | 0 | 3 | −0.80 | 0.640 | 1.27 | 1.604 |  |
|  | 0.80 | 1.73 |  | 2.400 |  | 14.933 |  | s   0.787   SD   0.400   0.998
Cal t value   −3.249   CV   50.000   57.564
table value is 2.0484 at $t_{0.05}$ at 28 d.f Conclusion: More uniformity among drug group patients on account of drug consumption whereas less uniformity among placebo group patients.

Statistical Analysis - t test - DYSPNEA

Comparision of Dyspnea before and after taking drug

| Patients (n) | 0 day (x1) | 6th day (x2) | d = (x2 − x1) | d$^2$ | (x1 − Meanx1)$^2$ | (x2 − Meanx2)$^2$ |  |
|---|---|---|---|---|---|---|---|
| 1 | 0 | 0 | 0 | 0 | 4.551 | 0.751 | Hypothesis (H$_o$): After |
| 2 | 1 | 1 | 0 | 0 | 1.284 | 0.018 | consuming drug there is no |
| 3 | 2 | 1 | −1 | 1 | 0.018 | 0.018 | significant reduction. |
| 4 | 3 | 1 | −2 | 4 | 0.751 | 0.018 | Result: Ho rejected |
| 5 | 2 | 1 | −1 | 1 | 0.018 | 0.018 | Conclusion: It is concluded that |
| 6 | 2 | 1 | −1 | 1 | 0.018 | 0.018 | there is significant reduction after |
| 7 | 2 | 1 | −1 | 1 | 0.018 | 0.018 | consuming drug. |
| 8 | 2 | 1 | −1 | 1 | 0.018 | 0.018 | Co-eff of variation before and |
| 9 | 2 | 1 | −1 | 1 | 0.018 | 0.018 | after consuming drug. |
| 10 | 2 | 1 | −1 | 1 | 0.018 | 0.018 | Result: 1. More consistent (less |
| 11 | 2 | 1 | −1 | 1 | 0.018 | 0.018 | uniformity) in dyspnea before |
| 12 | 3 | 1 | −2 | 4 | 0.751 | 0.018 | taking drug. 2. Less |
| 13 | 3 | 1 | −2 | 4 | 0.751 | 0.018 | consistent (more uniformity) after |
| 14 | 3 | 1 | −2 | 4 | 0.751 | 0.018 | taking drug. |
| 15 | 3 | 0 | −3 | 9 | 0.751 | 0.751 |  |
|  | 2.13 | 0.87 | −19 | 33 | 9.733 | 1.733 |  |

Mean = Sum d/n   −1.267
(Mean)$^2$   1.604   SD   0.81   0.340
s   0.799   CV   37.76   39.22
Cal t   −6.141
table value is 2.1448 at $t_{0.05}$ at 14 d.f -continued

Statistical Analysis - t test - DYSPNEA

Comparison of Drug Vs Placebo at the end of the 6th day

| | Dyspnea grading | | Drug | | Placebo | | |
|---|---|---|---|---|---|---|---|
| Patients (n) | Drug (x1) | Placebo (x2) | x1 − Mean | (x1 − Mean)$^2$ | x2 − Mean | (x2 − Mean)$^2$ | |
| 1 | 0 | 0 | −0.87 | 0.751 | −1.80 | 3.240 | Hypothesis (H$_o$): After |
| 2 | 1 | 1 | 0.13 | 0.018 | −0.80 | 0.640 | consuming drug there is no |
| 3 | 1 | 1 | 0.13 | 0.018 | −0.80 | 0.640 | significant difference between |
| 4 | 1 | 0 | 0.13 | 0.018 | −1.80 | 3.240 | drug and placebo. |
| 5 | 1 | 1 | 0.13 | 0.018 | −0.80 | 0.640 | Result: Ho rejected |
| 6 | 1 | 1 | 0.13 | 0.018 | −0.80 | 0.640 | Conclusion: There is significant |
| 7 | 1 | 1 | 0.13 | 0.018 | −0.80 | 0.640 | differnce between drug and |
| 8 | 1 | 1 | 0.13 | 0.018 | −0.80 | 0.640 | placebo. |
| 9 | 1 | 3 | 0.13 | 0.018 | 1.20 | 1.440 | Co-eff of variation between |
| 10 | 1 | 3 | 0.13 | 0.018 | 1.20 | 1.440 | drug and placebo |
| 11 | 1 | 3 | 0.13 | 0.018 | 1.20 | 1.440 | Result: 1. More consistent in |
| 12 | 1 | 3 | 0.13 | 0.018 | 1.20 | 1.440 | drug. 2. Less consistent in |
| 13 | 1 | 3 | 0.13 | 0.018 | 1.20 | 1.440 | placebo. |
| 14 | 1 | 3 | 0.13 | 0.018 | 1.20 | 1.440 | |
| 15 | 0 | 3 | −0.87 | 0.751 | 1.20 | 1.440 | |
| | 0.87 | 1.80 | | 1.733 | | 20.400 | | s         0.889   SD   0.340   1.166
Cal t value  −2.875  CV   39.223  64.788
table value is 2.0484 at t$_{0.05}$ at 28 d.f Conclusion: More uniformity among drug group patients on account of drug consumption whereas less uniformity among placebo group patients.

Statistical Analysis - t test - RESPIRATION

Comparison of Respiration before and after taking drug

| Patients (n) | 0 day (x1) | 6th day (x2) | d = (x2 − x1) | d$^2$ | (x1 − Meanx1)$^2$ | (x2 − Meanx2)$^2$ | |
|---|---|---|---|---|---|---|---|
| 1 | 32 | 20 | −12 | 144 | 18.204 | 0.071 | Hypothesis (H$_o$): After |
| 2 | 28 | 20 | −8 | 64 | 0.071 | 0.071 | consuming drug there is no |
| 3 | 28 | 20 | −8 | 64 | 0.071 | 0.071 | significant reduction. |
| 4 | 28 | 20 | −8 | 64 | 0.071 | 0.071 | Result: Ho rejected |
| 5 | 28 | 24 | −4 | 16 | 0.071 | 18.204 | Conclusion: It is concluded that |
| 6 | 26 | 18 | −8 | 64 | 3.004 | 3.004 | there is significant reduction after |
| 7 | 28 | 20 | −8 | 64 | 0.071 | 0.071 | consuming drug. |
| 8 | 24 | 22 | −2 | 4 | 13.938 | 5.138 | Co-eff of variation before and |
| 9 | 28 | 20 | −8 | 64 | 0.071 | 0.071 | after consuming drug. |
| 10 | 28 | 20 | −8 | 64 | 0.071 | 0.071 | Result: 1. More consistent (less |
| 11 | 30 | 20 | −10 | 100 | 5.138 | 0.071 | uniformity) in respiration rate |
| 12 | 24 | 22 | −2 | 4 | 13.938 | 5.138 | before taking drug. 2. Less |
| 13 | 28 | 18 | −10 | 100 | 0.071 | 3.004 | consistent (more uniformity) after |
| 14 | 24 | 14 | −10 | 100 | 13.938 | 32.871 | taking drug. |
| 15 | 32 | 18 | −14 | 196 | 18.204 | 3.004 | |
| | 27.73 | 19.73 | −120 | 1112 | 86.933 | 70.933 | |

Mean = Sum d/n  −8.000
(Mean)$^2$        64.000   SD   2.41   2.175
s                3.295   CV   8.68   11.02
Cal t           −9.403
table value is 2.1448 at t$_{0.05}$ at 14 d.f

Comparison of Drug Vs Placebo at the end of the 6th day

| | Respiration grading | | Drug | | Placebo | | |
|---|---|---|---|---|---|---|---|
| Patients (n) | Drug (x1) | Placebo (x2) | x1 − Mean | (x1 − Mean)$^2$ | x2 − Mean | (x2 − Mean)$^2$ | |
| 1 | 20 | 20 | 0.27 | 0.071 | −2.93 | 8.604 | Hypothesis (H$_o$): After |
| 2 | 20 | 20 | 0.27 | 0.071 | −2.93 | 8.604 | consuming drug there is no |
| 3 | 20 | 24 | 0.27 | 0.071 | 1.07 | 1.138 | significant difference between |
| 4 | 20 | 24 | 0.27 | 0.071 | 1.07 | 1.138 | drug and placebo. |
| 5 | 24 | 20 | 4.27 | 18.204 | −2.93 | 8.604 | Result: Ho rejected |
| 6 | 18 | 22 | −1.73 | 3.004 | −0.93 | 0.871 | Conclusion: There is significant |

-continued

| | | | Statistical Analysis - t test - RESPIRATION | | | | |
|---|---|---|---|---|---|---|---|
| 7 | 20 | 20 | 0.27 | 0.071 | −2.93 | 8.604 | diffrence between drug and |
| 8 | 22 | 20 | 2.27 | 5.138 | −2.93 | 8.604 | placebo. |
| 9 | 20 | 24 | 0.27 | 0.071 | 1.07 | 1.138 | Co-eff of variation between |
| 10 | 20 | 24 | 0.27 | 0.071 | 1.07 | 1.138 | drug and placebo |
| 11 | 20 | 26 | 0.27 | 0.071 | 3.07 | 9.404 | Result: 1. More variable (no of |
| 12 | 22 | 26 | 2.27 | 5.138 | 3.07 | 9.404 | respirations) in drug. 2. Less |
| 13 | 18 | 24 | −1.73 | 3.004 | 1.07 | 1.138 | variable in placebo. |
| 14 | 14 | 26 | −5.73 | 32.871 | 3.07 | 9.404 | |
| 15 | 18 | 24 | −1.73 | 3.004 | 1.07 | 1.138 | |
| | 19.73 | 22.93 | | 70.933 | | 78.933 | | s        2.314   SD   2.175   2.294
Cal t value  −3.788   CV   11.020   10.003
table value is 2.0484 at $t_{0.05}$ at 28 d.f Conclusion: More uniformity among drug group patients on account of drug consumption whereas less uniformity among placebo group patients.

| | | | Statistical Analysis - t test - PULSE | | | |
|---|---|---|---|---|---|---|
| | | | Comparision of Pulse before and after taking drug | | | |
| Patients (n) | 0 day (x1) | 6th day (x2) | d = (x2 − x1) | $d^2$ | $(x1 - \text{Meanx1})^2$ | $(x2 - \text{Meanx2})^2$ | |
| 1 | 128 | 94 | −34 | 1156 | 170.738 | 21.160 | Hypothesis ($H_o$): After |
| 2 | 110 | 96 | −14 | 196 | 24.338 | 43.560 | consuming drug there is no |
| 3 | 120 | 88 | −32 | 1024 | 25.671 | 1.960 | significant reduction. |
| 4 | 110 | 88 | −22 | 484 | 24.338 | 1.960 | Result: Ho rejected |
| 5 | 120 | 92 | −28 | 784 | 25.671 | 6.760 | Conclusion: It is concluded that |
| 6 | 120 | 96 | −24 | 576 | 25.671 | 43.560 | there is significant reduction after |
| 7 | 120 | 94 | −26 | 676 | 25.671 | 21.160 | consuming drug. |
| 8 | 120 | 88 | −32 | 1024 | 25.671 | 1.960 | Co-eff of variation before and |
| 9 | 98 | 86 | −12 | 144 | 286.738 | 11.560 | after consuming drug. |
| 10 | 110 | 90 | −20 | 400 | 24.338 | 0.360 | Result: 1. Less consistent in |
| 11 | 120 | 90 | −30 | 900 | 25.671 | 0.360 | pulse rate before taking drug. 2. |
| 12 | 120 | 86 | −34 | 1156 | 25.671 | 11.560 | More consistent after taking drug. |
| 13 | 110 | 85 | −25 | 625 | 24.338 | 19.360 | |
| 14 | 120 | 88 | −32 | 1024 | 25.671 | 1.960 | |
| 15 | 98 | 80 | −18 | 324 | 286.738 | 88.360 | |
| | 114.93 | 89.40 | −383 | 10493 | 1046.933 | 275.600 | |

Mean = Sum d/n    −25.533
$(\text{Mean})^2$    651.951   SD   8.35   4.286
s                 7.140   CV   7.27   4.79
Cal t             −13.850
table value is 2.1448 at $t_{0.05}$ at 14 d.f

| | | Comparison of Drug Vs Placebo at the end of the 6th day | | | | |
|---|---|---|---|---|---|---|
| | Pulse grading | | Drug | | Placebo | |
| Patients (n) | Drug (x1) | Placebo (x2) | x1 − Mean | $(x1 - \text{Mean})^2$ | x2 − Mean | $(x2 - \text{Mean})^2$ | |
| 1 | 94 | 84 | 4.60 | 21.160 | −13.60 | 184.96 | Hypothesis ($H_o$): After |
| 2 | 96 | 84 | 6.60 | 43.560 | −13.60 | 184.96 | consuming drug there is no |
| 3 | 88 | 90 | −1.40 | 1.960 | −7.60 | 57.76 | significant difference between |
| 4 | 88 | 92 | −1.40 | 1.960 | −5.60 | 31.36 | drug and placebo. |
| 5 | 92 | 96 | 2.60 | 6.760 | −1.60 | 2.56 | Result: Ho rejected |
| 6 | 96 | 92 | 6.60 | 43.560 | −5.60 | 31.36 | Conclusion: There is significant |
| 7 | 94 | 86 | 4.60 | 21.160 | −11.60 | 134.56 | diffrence between drug and |
| 8 | 88 | 92 | −1.40 | 1.960 | −5.60 | 31.36 | placebo. |
| 9 | 86 | 100 | −3.40 | 11.560 | 2.40 | 5.76 | Co-eff of variation between |
| 10 | 90 | 118 | 0.60 | 0.360 | 20.40 | 416.16 | drug and placebo |
| 11 | 90 | 120 | 0.60 | 0.360 | 22.40 | 501.76 | Result: 1. More consistent (less |
| 12 | 86 | 114 | −3.40 | 11.560 | 16.40 | 268.96 | variable) in drug. 2. Less |
| 13 | 85 | 102 | −4.40 | 19.360 | 4.40 | 19.36 | consistent in placebo (More |

-continued

Statistical Analysis - t test - PULSE

| 14 | 88 | 94 | −1.40 | 1.960 | −3.60 | 12.96 | variable) |
| 15 | 80 | 100 | −9.40 | 88.360 | 2.40 | 5.76 | |
| | 89.40 | 97.60 | | 275.600 | | 1889.6 | | s            8.794  SD  4.286  11.224
Cal t value  −2.554  CV  4.795  11.500
table value is 2.0484 at $t_{0.05}$ at 28 d.f Conclusion: More uniformity among drug group patients on account of drug consumption whereas less uniformity among placebo groups patients.

I claim:

1. A herbal composition, comprising:
   (a) 75–90% by weight of material extracted with a polar solvent from plants belonging to the following genera:
   Bryonia,
   and Drosera,
   and
   (b) the balance by weight being antimony potassium tartarate, wherein said polar solvent is selected from the group consisting of water, alcohol, ketone, ester, amide, sulfoxide, nitryle and a mixture thereof.

2. The herbal composition of claim 1, wherein the proportion by weight of material extracted from the plants is as follows:

| Bryonia | 35% |
| Drosera | 55%, and |
| antimony potassium tartarate | 10%. |

3. The herbal composition of claim 1, further comprising up to about plant material extracted with a polar solvent from Ipecacuanha species, wherein proportion by weight of all extracted plant materials is 75–90%, and wherein the polar solvent for extraction of Ipecacuanha species is selected from the group consisting of water, alcohol, ketone, ester, amide, sulfoxide, nitryl and a mixture thereof.

4. The herbal composition of claim 1, wherein the material extracted from each of the plants and the antimony potassium tartarate are equally 25% by weight.

5. The composition of claim 4, wherein said polar solvent is ethanol, methanol, propanol, acetone, ethyl acetate and a mixture thereof.

6. The herbal composition of claim 5, wherein said polar solvent is ethanol.

7. A herbal composition, comprising:
   (a) 75–90% by weight of dry material obtained from an ethanolic extract of plants belonging to the following genera:
   Bryonia,
   and Drosera,
   and
   (b) the balance by weight being antimony potassium tartarate,
   wherein said polar solvent is selected from the group consisting of water, alcohol, ketone, ester, amide, sulfoxide, nitryle and a mixture thereof.

8. The herbal composition of claim 7, wherein the proportion by weight of material extracted from the plants is as follows:

| Bryonia | 35% |
| Drosera | 55%, and |
| antimony potassium tartarate | 10%. |

9. The herbal composition of claim 7, further comprising plant material extracted with a polar solvent from Ipecacuanha species, wherein proportion by weight of all extracted plant materials is 75–90%, and wherein the polar solvent for extraction of Ipecacuanha species is selected from the group consisting of water, alcohol, ketone, ester, amide, sulfoxide, nitryl and a mixture thereof.

10. A herbal composition, comprising:
    (a) 75–90% by weight of dry material obtained from an ethanolic extract of plants belonging to the following genera:
    Bryonia
    Drosera,
    and Ipecacuanha,
    and
    (b) 10–25% by weight of antimony potassium tartarate.

11. The herbal composition of claim 10, wherein the material extracted from each of the plant genera and the antimony potassium tartarate are equally 25% by weight.

12. The herbal composition of claim 10, wherein the proportion of constituents is as follows:

| Bryonia | 35% |
| Ipecacuanha | 25% |
| and Drosera, | 30% |
| and | |
| antimony potassium tartarate | 10%. |

13. The herbal composition of claim 6, being formulated as a capsule, tablet or in honey.

14. The herbal composition of claim 9, being formulated as a capsule, tablet or in honey.

15. The herbal composition of claim 12, being formulated as a capsule, tablet or in honey.

* * * * *